United States Patent
Jiang et al.

(10) Patent No.: US 10,572,723 B2
(45) Date of Patent: Feb. 25, 2020

(54) ACTIVITY DETECTION BY JOINT HUMAN AND OBJECT DETECTION AND TRACKING

(71) Applicant: Futurewei Technologies, Inc., Plano, TX (US)

(72) Inventors: Wei Jiang, San Jose, CA (US); Lyndon Scott Kennedy, San Francisco, CA (US); Wei Wang, San Jose, CA (US)

(73) Assignee: Futurewei Technologies, Inc., Plano, TX (US)

( * ) Notice: Subject to any disclaimer, the term of this patent is extended or adjusted under 35 U.S.C. 154(b) by 152 days.

(21) Appl. No.: 15/835,195

(22) Filed: Dec. 7, 2017

(65) Prior Publication Data

US 2019/0180090 A1 Jun. 13, 2019

(51) Int. Cl.
*H04N 7/18* (2006.01)
*G06K 9/00* (2006.01)
(Continued)

(52) U.S. Cl.
CPC ...... *G06K 9/00342* (2013.01); *A63B 24/0062* (2013.01); *G06K 9/00771* (2013.01);
(Continued)

(58) Field of Classification Search
USPC ....... 382/100, 103, 106–107, 154, 155, 162, 382/168, 173, 181, 199, 209, 220, 224,
(Continued)

(56) References Cited

U.S. PATENT DOCUMENTS

2014/0347475 A1* 11/2014 Divakaran ......... G06K 9/00771
 348/135
2015/0213702 A1* 7/2015 Kimmel ............... G08B 21/043
 382/103
(Continued)

OTHER PUBLICATIONS

Tobias Baumgartner et al "Tracking People and Their Objects", provided by the Computer Vision Founation. IEEE Xplore. 2013 p. 3658-3665. 2013.*

(Continued)

*Primary Examiner* — Seyed H Azarian
(74) *Attorney, Agent, or Firm* — Vierra Magen Marcus LLP

(57) ABSTRACT

A computing device includes a communication interface, a memory, and processing circuitry. The processing circuitry is coupled to the communication interface and to the memory and is configured to execute the operational instructions to perform various functions. The computing device is configured to process a video frame of a video segment on a per-frame basis and based on joint human-object interactive activity (HOIA) to generate a per-frame pairwise human-object interactive (HOI) feature based on a plurality of candidate HOI pairs. The computing device is also configured to process the per-frame pairwise HOI feature to identify a valid HOI pair among the plurality of candidate HOI pairs and to track the valid HOI pair through subsequent frames of the video segment to generate a contextual spatial-temporal feature for the valid HOI pair to be used in activity detection.

20 Claims, 9 Drawing Sheets

(51) Int. Cl.
  *G06K 9/46* (2006.01)
  *G06T 7/246* (2017.01)
  *A63B 24/00* (2006.01)

(52) U.S. Cl.
  CPC ............ *G06K 9/4628* (2013.01); *G06T 7/246* (2017.01); *G06T 2207/10004* (2013.01); *G06T 2207/10016* (2013.01); *G06T 2207/30196* (2013.01); *G06T 2207/30221* (2013.01)

(58) Field of Classification Search
  USPC ....... 382/232, 254, 274, 276, 285–291, 305, 382/312; 348/135; 713/168
  See application file for complete search history.

(56) References Cited

U.S. PATENT DOCUMENTS

| | | | | |
|---|---|---|---|---|
| 2016/0036786 | A1* | 2/2016 | Gandhi | H04W 12/06 713/168 |
| 2017/0116446 | A1* | 4/2017 | Sample | G06Q 30/0251 |

OTHER PUBLICATIONS

Tobias Baumgartner et al "Tracking people and Their Object" provide by the Computer Vision Foundation. IEEE Xplore. 2013, p. 3658-3665.2013.*

Akila, K. et al. Discriminative Human Action Recognition using HOI Descriptor and Key Poses. International Conference on Science, Engineering and Management Research,(ICSEMR 2014), 6 pages.

Alessandro Prest et al. Explicit Modeling of Human-Object Interactions in Realistic Videos, IEEE Transactions on Pattern Analysis and Machine Intelligence, vol. 35, No. 4, Apr. 2013. pp. 835-848.

Yu-Wei Chao et al. HICO: A Benchmark for Recognizing Human-Object Interactions in Images, 2015 IEEE International Conference on Computer Vision. 2015 IEEE. pp. 1017-1025.

Abhinav Gupta et al. Observing Human-Object Interactions Using Spatial and Functional Compatibility for Recognition, IEEE Transactions on Pattern Analysis and Machine Intelligence, vol. 31, No. 10, Oct. 2009. pp. 1775-1789.

International Search Report dated Feb. 28, 2019, in PCT Application No. PCT/CN2018/119516, 8 pages.

* cited by examiner

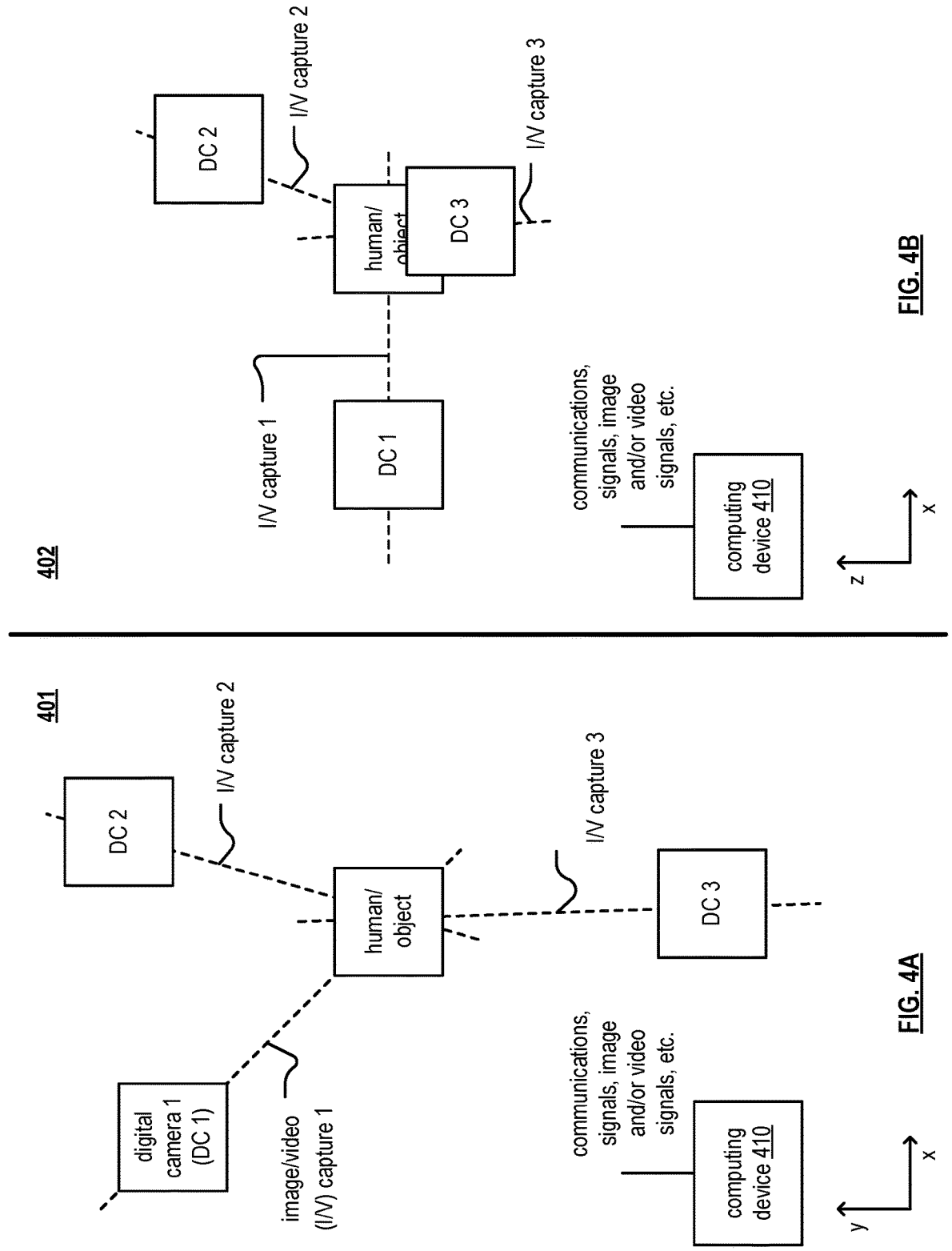

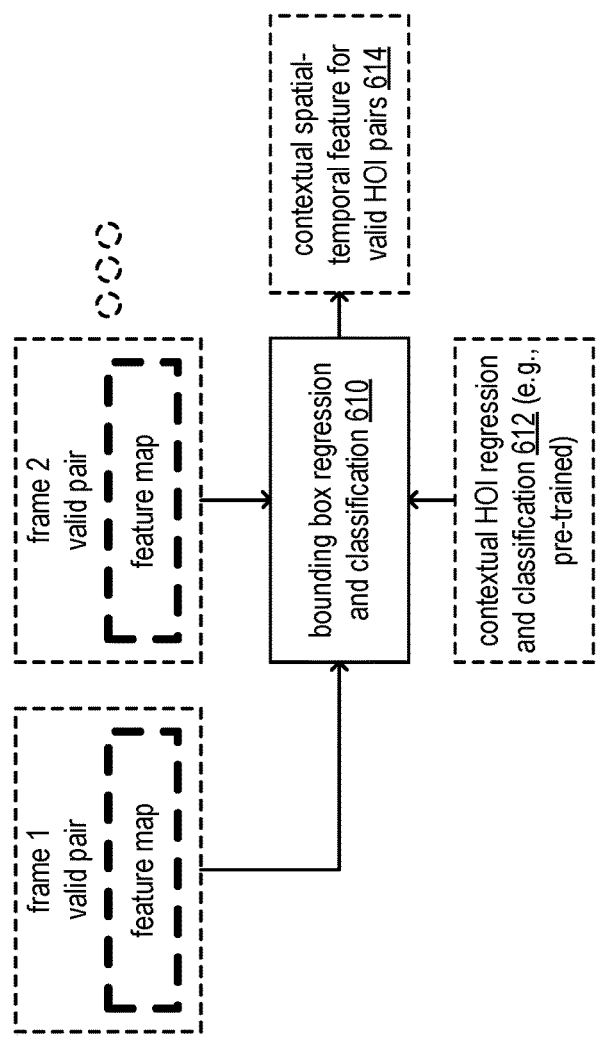
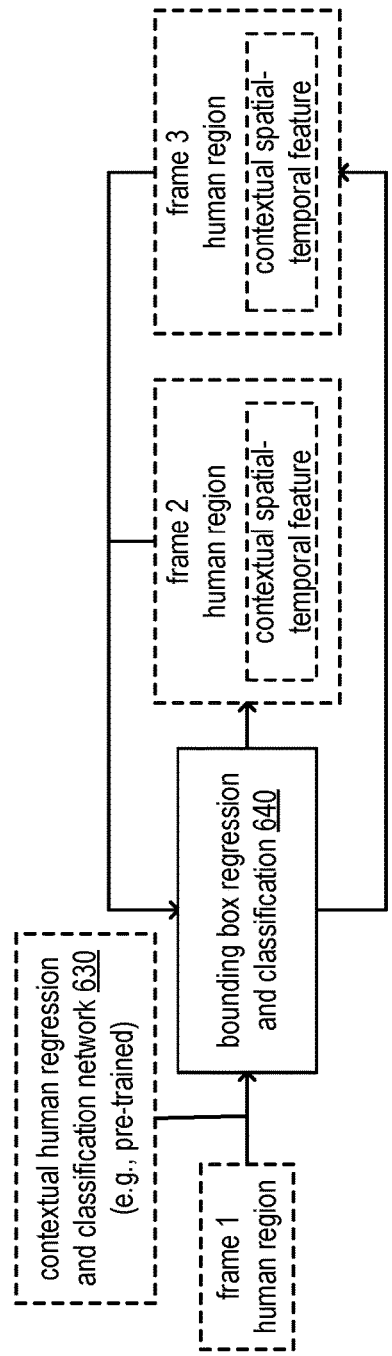
FIG. 6A
FIG. 6B

FIG. 8A

801 start receiving a video segment (e.g., via an interface of a computing device, via a digital camera (DC), from memory, etc.) 810 processing a video frame of the video segment on a per-frame basis and based on joint human-object interactive activity (HOIA) to generate a per-frame pairwise human-object interactive (HOI) feature based a plurality (or one or more) candidate HOI pairs 820 processing the per-frame pairwise HOI feature to identify a valid HOI pair among the plurality (or one or more) candidate HOI pairs 830 tracking a valid HOI pair through subsequent frames of the video segment to generate a contextual spatial-temporal feature for the valid HOI pair to be used in activity detection (and/or learning, monitoring, logging, etc.) 840 end

FIG. 8B

802 start processing a video frame to identify a detected human region in accordance with human detection based on a pre-trained human detection network 811 processing a video frame to identify a detected object region in accordance with object detection based on a pre-trained object detection network 821 end

FIG. 8C

803 start processing a detected human region and a detected object human region within a video frame to generate candidate human-object region pair(s) 812 generating a per-frame pairwise HOI feature based on a human region bounding box and a human feature vector associated with the detected human region and an object region bounding box and an object feature vector associated with the detected object region and 822 combined human-object feature vector 824 end

ACTIVITY DETECTION BY JOINT HUMAN AND OBJECT DETECTION AND TRACKING

TECHNICAL FIELD

The present disclosure relates generally to video and/or image processing; and, more particularly, to detection and tracking of human and object elements in accordance with such video and/or image processing.

BACKGROUND OF THE INVENTION

The prior art includes various methods for performing video and/or image processing. Generally speaking, activity detection within such prior art approaches is based on processing whole frames of image and/or video content, and classification of traditional human activity performed therein is made into an activity category. For example, image frames of such video (e.g., a sequence of video frames) are classified into different action categories based on features within the image frames.

Such prior art approaches typically operate based generally on individual human activities and particularly on a person's position within an image frame. Such prior art processing is based on the entirety of an image frame, and the entire image frame is processed based on some type of classifier including performing direct analysis of the whole frame. Such prior art processing can be extremely intensive and burdensome in terms of consumption of processing resources. There exists significant room in the prior art for improvement in the manner by which video and/or image processing may be performed.

SUMMARY

According to various aspects of the present disclosure, there is provided video processing that is based on joint human-object interactive activity (HOIA) learning, detection, and tracking. The interaction and relationship between a human and an object (or one or more objects) is determined jointly by automatically determining human-object pair association. This joint human-object interactive activity (HOIA) learning, detection, and tracking is very fast in terms of computational speed and also operates with very efficient network training with limited data by knowledge transfer such as by using pre-trained human and object detectors.

According to a first aspect of the present disclosure, there is provided a computing device that includes a communication interface configured to interface and communicate with a communication network, memory that stores operational instructions, and processing circuitry coupled to the communication interface and to the memory. The processing circuitry is configured to execute the operational instructions to perform various functions, operations, processes, etc. The computing device is configured to process a video frame of a video segment on a per-frame basis and based on joint human-object interactive activity (HOIA) to generate a per-frame pairwise human-object interactive (HOI) feature based on a plurality of candidate HOI pairs. The computing device is also configured to process the per-frame pairwise HOI feature to identify a valid HOI pair among the plurality of candidate HOI pairs and track the valid HOI pair through subsequent frames of the video segment to generate a contextual spatial-temporal feature for the valid HOI pair to be used in activity detection.

According to a second aspect of the present disclosure, there is provided a computer readable storage device that includes a non-transitory computer readable medium storing computer instructions that, when executed by one or more processing circuitries cause the one or more processing circuitries to perform various steps, functions, operations, processes, etc. The computer instructions cause the one or more processing circuitries to process a video frame of a video segment on a per-frame basis and based on joint human-object interactive activity (HOIA) to generate a per-frame pairwise human-object interactive (HOI) feature based on a plurality of candidate HOI pairs and also to process the per-frame pairwise HOI feature to identify a valid HOI pair among the plurality of candidate HOI pairs. Also, the computer instructions cause the one or more processing circuitries to track the valid HOI pair through subsequent frames of the video segment to generate a contextual spatial-temporal feature for the valid HOI pair to be used in activity detection According to a third aspect of the present disclosure, there is provided a method for execution by a computing device that includes receiving a video segment via an interface of the computing device that is configured to interface and communicate with a communication network, and processing a video frame of the video segment on a per-frame basis and based on joint human-object interactive activity (HOIA) to generate a per-frame pairwise human-object interactive (HOI) feature based on a plurality of candidate HOI pairs. The method also includes processing the per-frame pairwise HOI feature to identify a valid HOI pair among the plurality of candidate HOI pairs, and tracking the valid HOI pair through subsequent frames of the video segment to generate a contextual spatial-temporal feature for the valid HOI pair to be used in activity detection.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

FIG. 4A and FIG. 4B are diagrams of embodiments of a computing device performs processing based on captured images and/or video content by one or more digital cameras (DCs).

FIG. 6A is a diagram illustrating an embodiment of contextual spatial-temporal human-object interactive (HOI) tracking.

FIG. 6B is a diagram illustrating an embodiment of contextual spatial-temporal human tracking.

FIG. 8A is a diagram illustrating an embodiment of a method for execution by one or more computing devices.

FIG. 8B is a diagram illustrating another embodiment of a method for execution by one or more computing devices.

FIG. 8C is a diagram illustrating another embodiment of a method for execution by one or more computing devices.

DETAILED DESCRIPTION

It should be understood at the outset that, although illustrative implementations of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The present disclosure to provide methods and structures that enable image and/or video processing as may be performed using a computing device, a communication device, a method, and other platforms that includes targeted spatial-temporal joint human and object feature learning for each individual HOIA as a context and that also includes context (HOIA) dependent human tracking for contextual spatial-temporal human feature extraction. Such image and/or video processing also includes context (HOIA) dependent human object interaction (HOI) tracking for contextual spatial-temporal HOI feature extraction. This provides for effective HOIA detection by considering both spatial-temporal human feature and spatial-temporal HOI feature through implicit HOI relationship modeling. Also, one or more pre-trained human and object detectors may be used to transfer knowledge learned from large scale human and object detection data to the current activity detection task.

Figure 1:
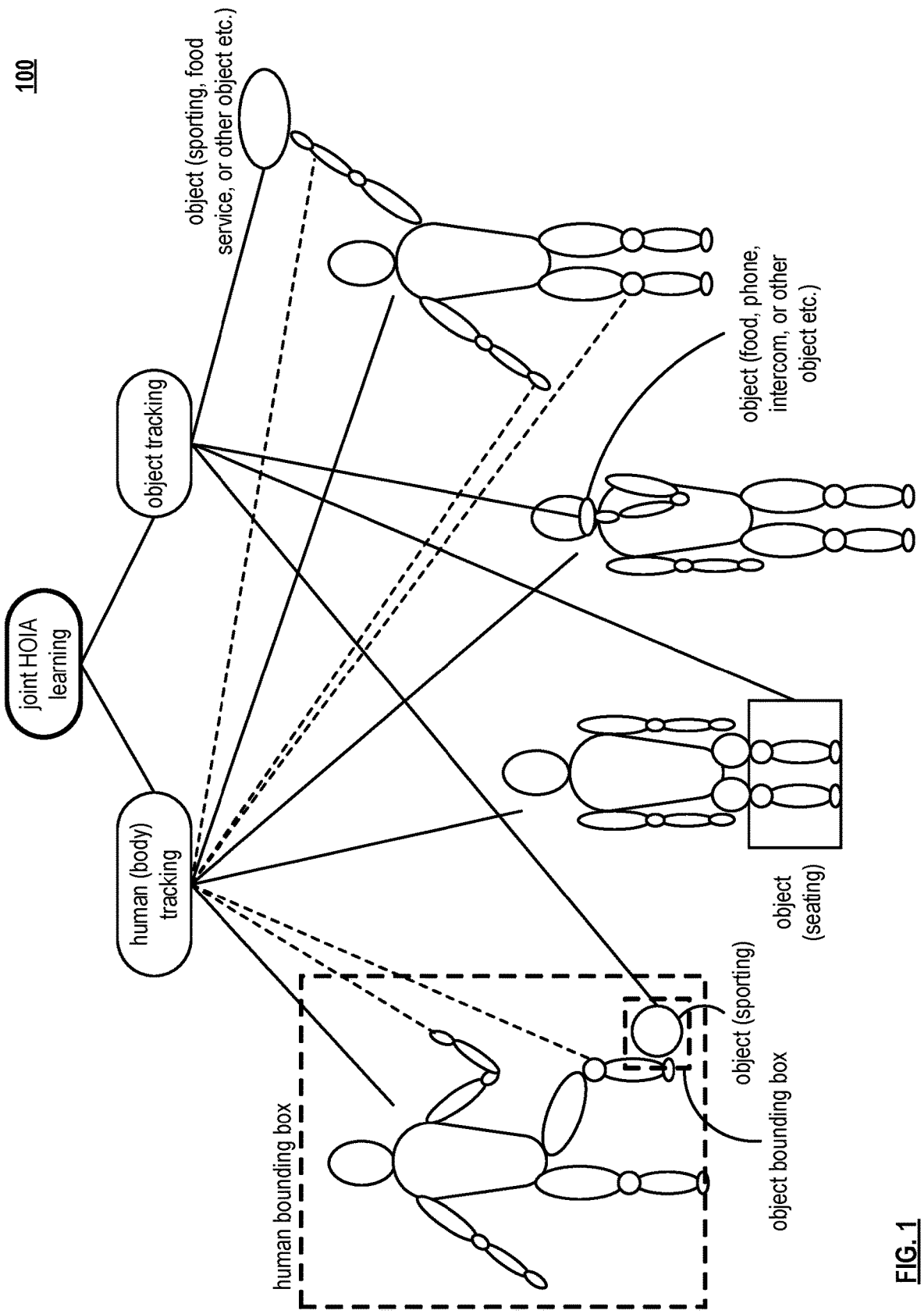
FIG. 1 is a diagram illustrating an embodiment of a joint human-object interactive activity (HOIA) learning as may be performed by a computing device, a communication device, and/or method.

FIG. 1 is a diagram illustrating an embodiment 100 of a joint human-object interactive activity (HOIA) learning as may be performed by a computing device, a communication device, and/or method. A novel approach is presented herein by which human body tracking is associated with object tracking in accordance with joint human-object interactive activity (HOIA) learning and processing. Various aspects, embodiments, and/or examples, and their equivalents, presented herein operate by performing joint processing of one or more humans and one or more objects. Such processing is based on HOIA detection based on joint human and object detection and tracking. Such operations include targeted spatial-temporal joint human and object feature learning for each individual HOIA as a context and also include context (HOIA) dependent human tracking for contextual spatial-temporal human feature extraction. Such operations also include context (HOIA) dependent human object interaction (HOI) tracking for contextual spatial-temporal HOI feature extraction. This provides for effective HOIA detection by considering both spatial-temporal human feature and spatial-temporal HOI feature through implicit HOI relationship modeling. Also, one or more pre-trained human and object detectors may be used to transfer knowledge learned from large scale human and object detection data to the current activity detection task.

Referring to the diagram, joint human (body) tracking and object tracking are performed in accordance with joint HOIA learning. For example, activity detection and recognition of one or more humans and one or more objects is performed in accordance with joint monitoring. Specific individuals and specific activities may be identified and logged over time.

In an example of operation and implementation, a computing device includes a communication interface configured to interface and communicate with a communication network, memory that stores operational instructions and processing circuitry coupled to the communication interface and to the memory. The processing circuitry is configured to execute the operational instructions to perform various functions, operations, processes, etc. In some examples, note that such a processing circuitry may alternatively be implemented as and/or referred to as a judging unit, a determining unit, and/or an executing unit. In an example, the computing device is configured to process a video frame of a video segment on a per-frame basis and based on joint human-object interactive activity (HOIA) to generate a per-frame pairwise human-object interactive (HOI) feature based on a plurality of candidate HOI pairs. Broadly speaking, HOIA may be understood as an activity that is particularly related to a particular person and how that particular person interacts with an object. Such HOIA may be viewed in terms of a number of factors including a person, an object, and/or an activity. In some specific examples, this includes a specific person, a specific object, and/or a specific activity. One particular example of HOIA includes a person interacting an object based on an activity. Some examples may include a person interacting with a glass to consume a beverage, a person interacting with a sporting ball to participate in a sport, a person interacting with a chair and/or television to consume audio and/or video media, etc. In general, such HOIA may also be viewed to include one or more persons interacting with one or more objects based on one or more activities.

The computing device is also configured to process the per-frame pairwise HOI feature to identify a valid HOI pair among the plurality of candidate HOI pairs. In some examples, a per-frame pairwise HOI feature includes 3-dimensional (3-D) data associated with a person and an object within a frame (e.g., the 3-D data associated with location of the person and the 3-D data associated with location of the object). In some examples, this information is provided as output from processing of the frame such as in accordance with that as performed by a neural network appropriately tailored to do so. Such 3-D related information may be associated a feature map as also described herein. Also, in some particular examples, a per-frame pairwise HOI feature is associated with a particular person per-frame pairwise HOI pair (e.g., a pair that includes a particular person and a particular object).

The computing device is also configured to track the valid HOI pair through subsequent frames of the video segment to generate a contextual spatial-temporal feature for the valid HOI pair to be used in activity detection. For example, with respect to a person and an object associated with the valid HOI pair, the corresponding per-frame pairwise HOI feature is tracked through multiple frames to generate the contextual spatial-temporal feature. As an example, the 3-D data associated with location of the person and the 3-D data associated with location of the object are tracked, as being a valid HOI pair, through multiple frames to generate the contextual spatial-temporal feature. An example of a contextual spatial-temporal feature includes the data (e.g., the 3-D data) associated with person and an object based on performing activity through multiple frames. Additional examples, embodiments, and details are described below.

Figure 2:
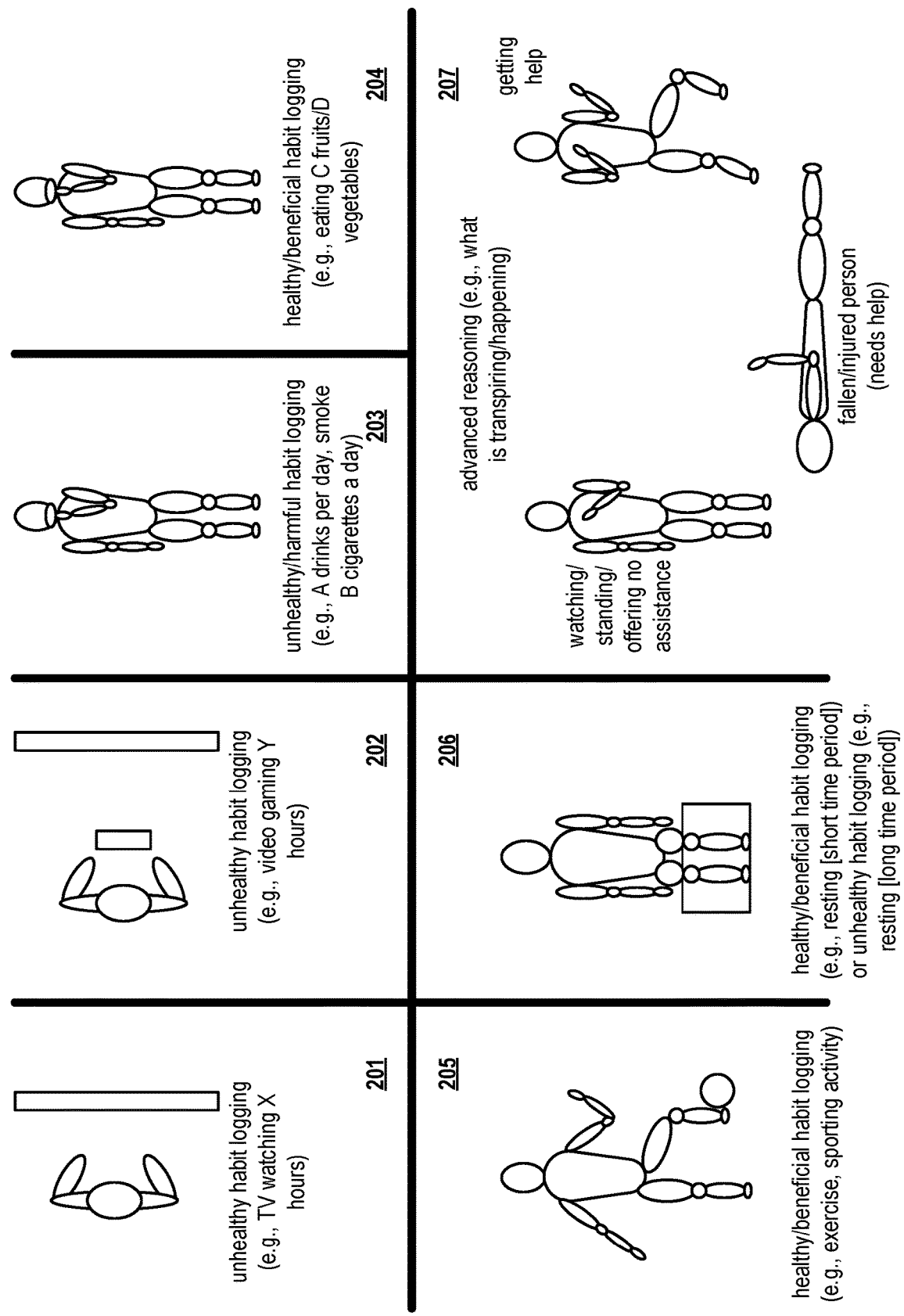
FIG. 2 is a diagram illustrating various examples of activity recognition use cases.

FIG. 2 is a diagram illustrating various examples 201, 202, 203, 204, 205, 206, and 207 of activity recognition use cases. The joint HOIA learning as described herein may be applied to any of a number of use cases in accordance with detecting, tracking, monitoring, logging, etc. various human activities in accordance with various objects. Such human activities may be of various types including healthy, unhealthy, harmful, beneficial, and/or other types.

For example, unhealthy habit logging 201 is associated with a human performing TV watching for X number of hours a day, where X hours is some threshold number of hours (e.g., 6 hours, 8 hours, etc.) at or above which such prolonged TV watching deemed to be unhealthy. Unhealthy habit logging 202 is associated with a human engaging in video gaming for Y number of hours a day, where Y hours is some threshold number of hours (e.g., 4 hours, 10 hours, etc.) at or above which such prolonged video gaming is deemed to be unhealthy.

Unhealthy and/or harmful habit logging 203 is also associated with a human engaging in some unhealthy and/or harmful activity. One example includes a human consuming A drinks (e.g., alcoholic drinks, sugary drinks, etc.) per day, where A drinks is some threshold number of drinks (e.g., 8 drinks, 12 drinks, etc.) at or above which such a number of drinks consumed per day is deemed to be unhealthy and/or harmful.

Healthy and/or beneficial habit logging 204 is associated with a human engaging in some healthy and/or beneficial activity. One example includes a human eating a certain number and/or type of A drinks healthy and/or beneficial food items (e.g., eating fruits, vegetables, etc., etc.) per day, where C fruits and/or D vegetables is some threshold number of drinks (e.g., 1 banana, 2 salads, etc.) at or above which such a number of healthy and/or beneficial food items consumed per day is deemed to be healthy and/or beneficial.

Healthy and/or beneficial habit logging 204 is also associated with a human engaging in some healthy and/or beneficial activity. One example includes a human engaging in exercise and/or sporting activity (e.g., such as including a sporting object such as a soccer ball and/or any other object employed within other types of sporting activities). For example, engaging in exercise and/or sporting activity certain amount of time a day (e.g., a minimum of 30, 60, etc. minutes a day) is deemed to be healthy and/or beneficial.

Discriminative healthy and/or beneficial habit logging or unhealthy and/or harmful habit logging 204 is also associated with a human engaging in some activity that is deemed healthy and/or beneficial or unhealthy and/or harmful based on the amount of time or duration of which such activity is performed. One example includes a human engaging in resting or sitting (e.g., such as on a bench, a chair, etc.). For example, engaging in resting or sitting for a relative small period of time per day (e.g., 5 minutes, 10 minutes, etc.) while being accompanied with exercise and/or sporting activity, such as in between various exercise and/or sporting activity sessions, is deemed to be healthy and/or beneficial by allowing the human body to recuperate and regenerate. Alternatively, engaging in resting or sitting for an extensive period of time per day (e.g., 4 hours, 10 hours, etc.) without any associated exercise and/or sporting activity is deemed to be healthy and/or beneficial.

In addition, such joint HOIA learning, tracking, detection, recognition, etc. may be performed in accordance with advanced reasoning 207 such as determine what is happening in a particular one or more video frames of a video sequence. Consider, for example, a situation where a first person has fallen and/or is injured laying on the floor or ground. The behavior or other people may be processed based on their activity within the one or more video frames of the video sequence. One person may be simply watching/standing and offering no assistance, and another person may be going to get help. Such processing of the one or more video frames of the video sequence may undergo processing for one or more different purposes. Examples of such purposes include action recognition (e.g., a person running, a person who has fallen/is falling, a person who is helping, a person who is watching), group activity recognition (e.g., one or more people rendering help to one or more other people), intention/social role actions (e.g., watching, getting help, comforting, etc.).

Figure 3A:
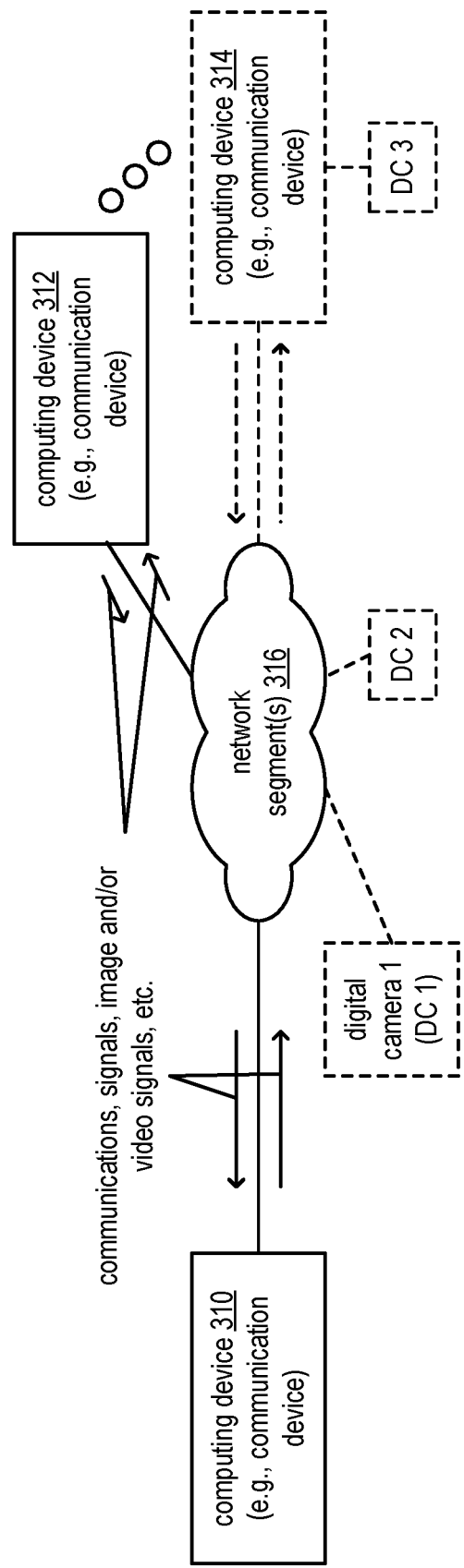
FIG. 3A is a diagram illustrating an embodiment of one or more communication systems.

FIG. 3A is a diagram illustrating an embodiment 301 of one or more communication systems. One or more network segments 316 provide communication inter-connectivity for at least two computing devices 310 and 312 (e.g., such computing devices may be implemented and operative to support communications with other computing devices in certain examples, and such computing devices may alternatively be referred to as communication devices in such situations including both computing device and communication device functionality and capability). Generally speaking, any desired number of communication devices are included within one or more communication systems (e.g., as shown by communication device 314). In addition, the one or more communication systems may include one or more digital cameras (e.g., a digital camera may alternatively be identified as a DC in certain of the diagrams). Such DCs may be implemented to be connected and/or coupled to the one or more network segments 316, connected and/or coupled to one of more of the computing devices 310-314, and/or integrated into one of more of the computing devices 310-314 and/or the one or more network segments 316. Such DCs are configured to perform image (e.g., photographic) and/or video capture within one or more directions, fields of view, perspectives, etc.

The various communication links within the one or more network segments 316 may be implemented using any of a variety of communication media including communication links implemented as wireless, wired, optical, satellite, microwave, and/or any combination thereof, etc. communication links. Also, in some instances, communication links of different types may cooperatively form a connection pathway between any two communication devices. Considering one possible example, a communication pathway between devices 310 and 312 may include some segments of wired communication links and other segments of optical communication links. Note also that the devices 310-314 may be of a variety of types of devices including stationary devices, mobile devices, portable devices, etc. and may support communications for any of a number of services or service flows including data, telephony, television, Internet, media, synchronization, etc.

In an example of operation and implementation, device 310 includes a communication interface to support communications with one or more of the other devices 312-314. In an example, the computing device 310 includes a communication interface configured to interface and communicate with a communication network (e.g., the one or more network segments 316), memory that stores operational instructions, and a processor coupled to the communication interface and to the memory. Note that such a processor may alternatively be implemented as and/or referred to as a judging unit, a determining unit, and/or an executing unit. The processor is configured to execute the operational instructions to perform various functions, operations, etc.

Note that the communication supported by the computing device 310 may be bidirectional/to and from the one or more of the other computing devices 312-314 or unidirectional (or primarily unidirectional) from the one or more of the other computing devices 312-314.

In one example, computing device 310 includes a processor that generates, modulates, encodes, etc. and transmits signals via a communication interface of the computing device 310 and also receives and processes, demodulates, decodes, etc. other signals received via the communication interface of the computing device 310 (e.g., received from other computing devices such as computing device 312, computing device 314, etc.).

In an example of operation, computing device 310, is configured to process a video frame of a video segment on a per-frame basis and based on joint human-object interactive activity (HOIA) to generate a per-frame pairwise human-object interactive (HOI) feature based on a plurality of candidate HOI pairs. The computing device 310 is also configured to process the per-frame pairwise HOI feature to identify a valid HOI pair among the plurality of candidate HOI pairs track the valid HOI pair through subsequent frames of the video segment to generate a contextual spatial-temporal feature for the valid HOI pair to be used in activity detection.

Figure 3B:
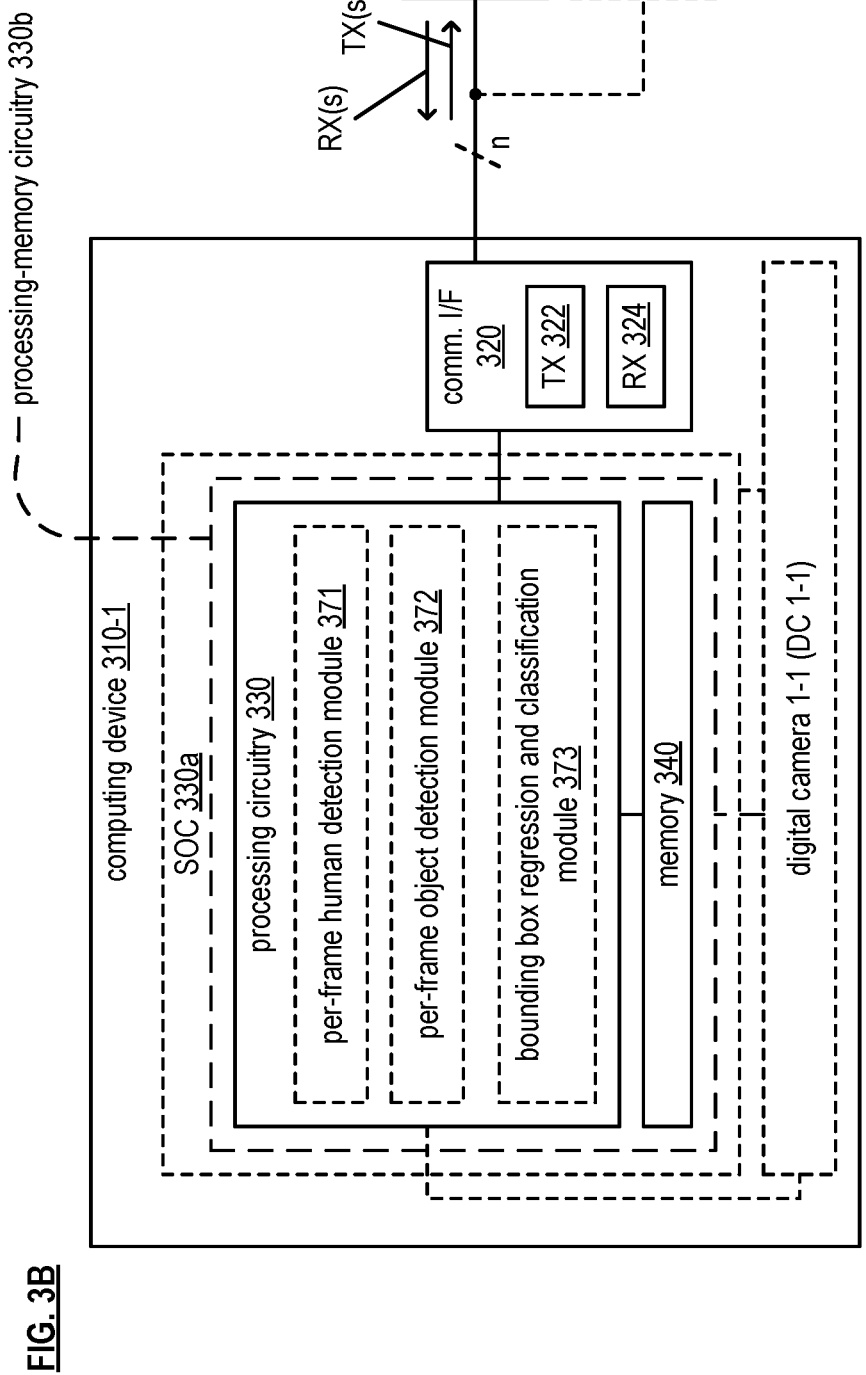
FIG. 3B is a diagram illustrating an embodiment of a computing device configured to be operate within one or more communication systems.

FIG. 3B is a diagram illustrating an embodiment 302 of a computing device 310-1 configured to be operate within one or more communication systems. The computing device 310-1 includes a communication interface 320 and processing circuitry 330. The computing device 310-1 may optionally include one or more digital cameras (DCs) (e.g., digital camera 1-1 (DC 1-1) and/or be in communication with one or more other DCs (e.g., DC 2-1). The communication interface 320 includes functionality of a transmitter 322 and a receiver 324 to support communications with one or more other devices within a communication system. In some examples, note that the transmitter 322 may alternatively be implemented as and/or referred to as a transmitting unit, and the receiver 324 may alternatively be implemented as and/or referred to as a receiving unit. The computing device 310-1 may also include memory 340 to store information including one or more signals generated by the computing device 310-1 or such information received from other devices (e.g., computing device 312) via one or more communication channels. For example, memory 340 may also include and store various operational instructions for use by the processing circuitry 330 in regards to the processing of messages and/or other received signals and generation of other messages and/or other signals including those described herein (e.g., image and/or video signals). Memory 340 may also store information including one or more types of encoding, one or more types of symbol mapping, concatenation of various modulation coding schemes, etc. as may be generated by the computing device 310-1 or such information received from other devices via one or more communication channels. The communication interface 320 supports communications to and from one or more other devices (e.g., computing device 312-1 and/or other computing devices). Memory 340 may also store information including one or more types of video and/or image processing in accordance with the various aspects, embodiments, and/or examples, and their equivalents, described herein.

Operation of the communication interface 320 may be directed by the processing circuitry 330 such that processing circuitry 330 transmits and receives signals (TX(s) and RX(s)) via the communication interface 320. Generally speaking, computing device 310-1 is able to support communications with one or more other computing device within one or more communication systems including computing device 312-2. In some examples, note that the processing circuitry 330 is implemented in hardware. In other examples, note that the processing circuitry 330 is implemented in hardware and software. In yet other examples, the processing circuitry 330 is implemented using one or more discrete components, application specific integrated circuits, processing circuitries, and/or processors executing appropriate software and the like or any combination thereof.

A computing device 310-1 (e.g., which may be any one of computing devices 310, 312, or 314 as with reference to FIG. 3A) is in communication with another computing device 312-1 (and/or any number of other wireless computing devices) via a communication medium. The computing device 310-1 includes a communication interface 320 to perform transmitting and receiving of at least one signal, symbol, packet, and/or frame, etc. (e.g., using a transmitter 322 and a receiver 324) (note that general reference to packet or frame may be used interchangeably).

Generally speaking, the communication interface 320 is implemented to perform any such operations of an analog front end (AFE) and/or physical layer (PHY) transmitter, receiver, and/or transceiver. Examples of such operations may include any one or more of various operations including conversions between the frequency and analog or continuous time domains (e.g., such as the operations performed by a digital to analog converter (DAC) and/or an analog to digital converter (ADC)), gain adjustment including scaling, filtering (e.g., in either the digital or analog domains), frequency conversion (e.g., such as frequency upscaling and/or frequency downscaling, such as to a baseband frequency at which one or more of the components of the computing device 310-1 operates), equalization, pre-equalization, metric generation, symbol mapping and/or de-mapping, automatic gain control (AGC) operations, and/or any other operations that may be performed by an AFE and/or PHY component within a computing device.

In some implementations, the computing device 310-1 also includes a processing circuitry 330, and an associated memory 340, to execute various operations including interpreting at least one signal, symbol, packet, and/or frame transmitted to computing device 312-1 and/or received from the computing device 312-1 and/or any other computing device. The computing devices 310-1 and 312-1 may be implemented using at least one integrated circuit in accordance with any desired configuration or combination of components, modules, etc. within at least one integrated circuit. Also, the computing devices 310 and/or 312 may each include one or more antennas for transmitting and/or receiving of at least one packet or frame wirelessly (e.g., computing device 310-1 may include m antennas, and computing device 312-1 may include n antennas, where m and n are positive integers).

Also, in some examples, note that one or more of the processing circuitry 330, the communication interface 320 (including the TX 322 and/or RX 324 thereof), and/or the memory 340 may be implemented in one or more "processing modules," "processing circuits," "processors," and/or "processing units" or their equivalents. Considering one example, a system-on-a-chip (SOC) 330a may be implemented to include the processing circuitry 330, the communication interface 320 (including the TX 322 and/or RX 324 thereof), and the memory 340 (e.g., SOC 330a being a multi-functional, multi-module integrated circuit that includes multiple components therein). Considering another example, processing-memory circuitry 330b may be implemented to include functionality similar to both the processing circuitry 330 and the memory 340 yet the communication interface 320 is a separate circuitry (e.g., processing-memory circuitry 330b is a single integrated circuit that performs functionality of a processing circuitry and a memory and is coupled to and also interacts with the communication interface 320).

Considering even another example, two or more processing circuitries may be implemented to include the processing circuitry 330, the communication interface 320 (including the TX 322 and/or RX 324 thereof), and the memory 340. In such examples, such a "processing circuitry," "processing circuitry," or "processing circuitries" (or "processor" or "processors") is/are configured to perform various operations, functions, communications, etc. as described herein. In general, the various elements, components, etc. shown within the computing device 310-1 may be implemented in any number of "processing modules," "processing circuits," "processors," and/or "processing units" (e.g., 1, 2, . . . , and generally using N such "processing modules," "processing circuits," "processors," and/or "processing units", where N is a positive integer greater than or equal to 1).

In some examples, the computing device 310-1 includes both processing circuitry 330 and communication interface 320 configured to perform various operations. In other examples, the computing device 310-1 includes SOC 330a configured to perform various operations. In even other examples, the computing device 310-1 includes processing-memory circuitry 330b configured to perform various operations. Generally, such operations include generating, transmitting, etc. signals intended for one or more other computing device (e.g., computing device 312-1) and receiving, processing, etc. other signals received for one or more other devices (e.g., computing device 312-1).

In some examples, note that the communication interface 320, which is coupled to the processing circuitry 330, is configured to support communications within a satellite communication system, a wireless communication system, a wired communication system, a fiber-optic communication system, and/or a mobile communication system (and/or any other type of communication system implemented using any type of communication medium or media). Any of the signals generated and transmitted and/or received and processed by the computing device 310-1 may be communicated via any of these types of communication systems.

Note that computing device 310-1 may be implemented to operate as any one or more of a satellite communication device, a wireless communication device, a wired communication device, a fiber-optic communication device, or a mobile communication device and implemented and/or operative within any one or more communication systems including a satellite communication system, a wireless communication system, a wired communication system, a fiber-optic communication system, or a mobile communication system, among other types of communication systems.

In an example of operation and implementation, a computing device includes a communication interface 320 configured to interface and communicate with a communication network, memory 340 that stores operational instructions, and processing circuitry 330 coupled to the communication interface 320 and to the memory 340.

The processing circuitry 330 is configured to execute the operational instructions to perform various functions, operations, and processes. The processing circuitry 330 is configured to process a video frame of a video segment on a per-frame basis and based on joint human-object interactive activity (HOIA) to generate a per-frame pairwise human-object interactive (HOI) feature based on a plurality of candidate HOI pairs and to process the per-frame pairwise HOI feature to identify a valid HOI pair among the plurality of candidate HOI pairs. The processing circuitry 330 is also configured to track the valid HOI pair through subsequent frames of the video segment to generate a contextual spatial-temporal feature for the valid HOI pair to be used in activity detection.

In some examples, the processing circuitry 330 includes a per-frame human detection module configured to process the video frame to identify a detected human region in accordance with human detection based on a pre-trained human detection network via the communication network. The processing circuitry 330 also includes a per-frame object detection module configured to process the video frame to identify a detected object region in accordance with object detection based on a pre-trained object detection network via the communication network.

In addition, in some alternative examples, the processing circuitry 330 is further configured to process the detected human region and the detected object region within the video frame to generate a plurality of candidate human-object region pairs. Then, for a candidate human-object region pair of the plurality of candidate human-object region pairs, the processing circuitry 330 is configured to generate the per-frame pairwise HOI feature based on a human region bounding box and a human feature vector associated with the detected human region and an object region bounding box and an object feature vector associated with the detected object region.

In other examples, the processing circuitry 330 is configured to process the detected human region and the detected object region within the video frame to generate a plurality of candidate human-object region pairs. Then, for a candidate human-object region pair of the plurality of candidate human-object region pairs, the processing circuitry 330 is configured to generate the per-frame pairwise HOI feature based on combined human-object location feature vector that is based on a human region bounding box and an object region bounding box and a combined human-object feature vector that is based on a human feature vector associated with the detected human region and an object feature vector associated with the detected object region.

Also, in some other examples, the processing circuitry 330 includes a bounding box regression and classification module configured to track the valid HOI pair through the subsequent frames of the video segment based on a pre-trained contextual human-object regression and classification network via the communication network and to output a tracked human region bounding box and a tracked object region bounding box associated with the valid HOI pair and the contextual spatial-temporal feature for the valid HOI pair.

Note that different respective HOI pairs of the plurality of candidate HOI pairs may be based on different respective sets of fully connected layers of a multi-domain network. For example, a first HOI pair of the plurality of candidate HOI pairs is based on a first context-specific set of fully connected layers of a multi-domain network in the subsequent frames of the video segment, and a second HOI pair of the plurality of candidate HOI pairs is based on a second context-specific set of fully connected layers of the multi-domain network in the subsequent frames of the video segment.

Within other specific examples, the processing circuitry 330 is configured to process the video frame of the video segment on the per-frame basis and based on human detection to generate a human region and to track the human region through subsequent frames of the video segment to generate another contextual spatial-temporal feature for the human region to be used in activity detection.

Note that any embodiment, example, variant, etc., and their equivalents, of a computing device may be implemented as any of a variety of computing devices including one or more of a home service robot, a long-term safety monitoring device, and/or a life recommendation device.

In some examples, the processing circuitry 330 includes one or more modules configured to perform one or more operations and/or support capability to perform one or more functionalities. Note that the functionality of any of the various modules as described herein may implemented by an appropriately configured processing circuitry 330 in certain examples. In one example, the processing circuitry 330 includes a per-frame human detection module 371 configured to process the video frame to identify a detected human region in accordance with human detection based on a pre-trained human detection network via the communication network. Also, in certain examples, the processing circuitry 330 includes a a per-frame object detection module 372 configured to process the video frame to identify a detected object region in accordance with object detection based on a pre-trained object detection network via the communication network. Also, in even other examples, the processing circuitry 330 includes a bounding box regression and classification module 373 configured to track the valid HOI pair through the subsequent frames of the video segment based on a pre-trained contextual human-object regression and classification network via the communication network and to output a tracked human region bounding box and a tracked object region bounding box associated with the valid HOI pair and the contextual spatial-temporal feature for the valid HOI pair.

In other examples, the processing circuitry 330 is configured to perform per-frame human detection processing of the video frame to identify a detected human region in accordance with human detection based on a pre-trained human detection network via the communication network, per-frame object detection processing of the video frame to identify a detected object region in accordance with object detection based on a pre-trained object detection network via the communication network, and/or bounding box regression and classification tracking of the valid HOI pair through the subsequent frames of the video segment based on a pre-trained contextual human-object regression and classification network via the communication network and to output a tracked human region bounding box and a tracked object region bounding box associated with the valid HOI pair and the contextual spatial-temporal feature for the valid HOI pair.

In alternative implementations, a computing device, module(s), or other component(s) includes a communication interface element, a processing element, a memory element, and optionally include one or more digital image office action video acquisition elements to perform and support the functionality and capability as described herein. For example, such an implementation includes a processing element configured to process a video frame of a video segment on a per-frame basis and based on joint human-object interactive activity (HOIA) to generate a per-frame pairwise human-object interactive (HOI) feature based on a plurality of candidate HOI pairs and to process the per-frame pairwise HOI feature to identify a valid HOI pair among the plurality of candidate HOI pairs. The processing element is also configured to process track the valid HOI pair through subsequent frames of the video segment to generate a contextual spatial-temporal feature for the valid HOI pair to be used in activity detection.

In other examples, a non-transitory computer readable medium storing computer instructions that, when executed by one or more processing circuitries (e.g., which may include processing circuitry 330), cause the one or more processing circuitries to perform various steps. In one example, the non-transitory computer readable medium storing computer instructions that, when executed by one or more processing circuitries cause the one or more processing circuitries (e.g., which may include processing circuitry 330) to perform the steps of process a video frame of a video segment on a per-frame basis and based on joint human-object interactive activity (HOIA) to generate a per-frame pairwise human-object interactive (HOI) feature based on a plurality of candidate HOI pairs, process the per-frame pairwise HOI feature to identify a valid HOI pair among the plurality of candidate HOI pairs, and track the valid HOI pair through subsequent frames of the video segment to generate a contextual spatial-temporal feature for the valid HOI pair to be used in activity detection.

In other examples, a computer readable storage device includes at least one memory section (e.g., which may include memory 340) that stores operational instructions to be executed by processing circuitry (e.g., which may include processing circuitry 330) of one or more computing devices that cause the one or more computing devices (e.g., which may include computing device 310-1) to process a video frame of a video segment on a per-frame basis and based on joint human-object interactive activity (HOIA) to generate a per-frame pairwise human-object interactive (HOI) feature based on a plurality of candidate HOI pairs, process the per-frame pairwise HOI feature to identify a valid HOI pair among the plurality of candidate HOI pairs, and track the valid HOI pair through subsequent frames of the video segment to generate a contextual spatial-temporal feature for the valid HOI pair to be used in activity detection. Note that such computer readable storage device includes a non-transitory computer readable storage device and/or non-transitory computer readable medium in certain examples.

In some other examples, the at least one memory section that stores operational instructions to be executed by processing circuitry of one or more computing devices further cause the one or more computing devices to perform per-frame human detection processing of the video frame to identify a detected human region in accordance with human detection based on a pre-trained human detection network via a communication network that is accessible via one or more communication interfaces of the one or more computing devices, and to perform per-frame object detection processing of the video frame to identify a detected object region in accordance with object detection based on a pre-trained object detection network via the communication network that is accessible via the one or more communication interfaces of the one or more computing devices.

Also, in some other examples, the at least one memory section that stores operational instructions to be executed by processing circuitry of one or more computing devices further cause the one or more computing devices to process the video frame to identify a detected human region in accordance with human detection based on a pre-trained human detection network via a communication network that is accessible via one or more communication interfaces of the one or more computing devices and to process the video frame to identify a detected object region in accordance with object detection based on a pre-trained object detection network via the communication network that is accessible via the one or more communication interfaces of the one or more computing devices. Note that such a HOI pair of the plurality of candidate HOI pairs is based on a unique context-specific set of fully connected layers of a multi-domain network in the subsequent frames of the video segment.

FIG. 4A and FIG. 4B are diagrams of embodiments 401 and 402 of a computing device performs processing based on captured images and/or video content by one or more digital cameras (DCs). These two diagrams are shown from two separate perspectives and include one or more DCs that perform image/video capture from one or more directions, perspectives, views, etc. of one or more humans and/or objects. A computing device 410 is configured to perform and support processing and functionality as described herein. In some examples, the computing device 410 in an implementation of one of the computing devices 310, 312, 314, or 310-1.

Referring to perspective of FIG. 4A, which is viewed in the xy plane of a 3D space having an xyz coordinate system, a digital camera 1 (DC1) is configured to perform image/video capture 1 from a first direction. If desired in alternative embodiments and/or examples, one or more additional DCs are configured to perform image/video capture from different directions (e.g., DC2 configured to perform image/video capture 2 from a second direction, DC3 configured to perform image/video capture 3 from a second direction, etc.).

Such different respective views from multiple DCs may be understood based on directional vectors extending from the multiple DC to the one or more humans and/or objects. For one example of operation, the principles of using triangulation may be employed when determining position of one or more humans and/or objects depicted in digital images captured by multiple DCs. For example, a projection of a first directional vector (DV1 proj.) from a first digital camera (DC1) extends from the first digital camera to the object. A projection of a second directional vector (DV2 proj.) from a second digital camera (DC2) extends from the second digital camera to the object. Additional directional vectors, associated with additional digital cameras, may also be employed. The directional vectors then undergo processing in a processing module to determine the intersection of the various directional vectors. The intersection of these directional vectors is the location of the object. Referring to perspective of FIG. 7B, this diagram is viewed in the xz plane of a 3D space having an xyz coordinate system. Note that as few as one DC may be used to perform image/video capture from a singular direction. In some examples, when multiple DCs are employed, the multiple respective image/video captures from the multiple DCs may undergo processing to provide additional confirmation, redundancy, verification, etc. of results from any one of the image/video captures from a single DC.

In general, any number of DCs (e.g., including as few as one DC) may be used to perform image/video capture. In addition, the various aspects, embodiments, and/or examples, and their equivalents, described herein may be applied to and performed in accordance with image and/or video content provided from any desired source including that which is received from another computing device such as via a communication system, one or more network segments, etc.

Figure 5:
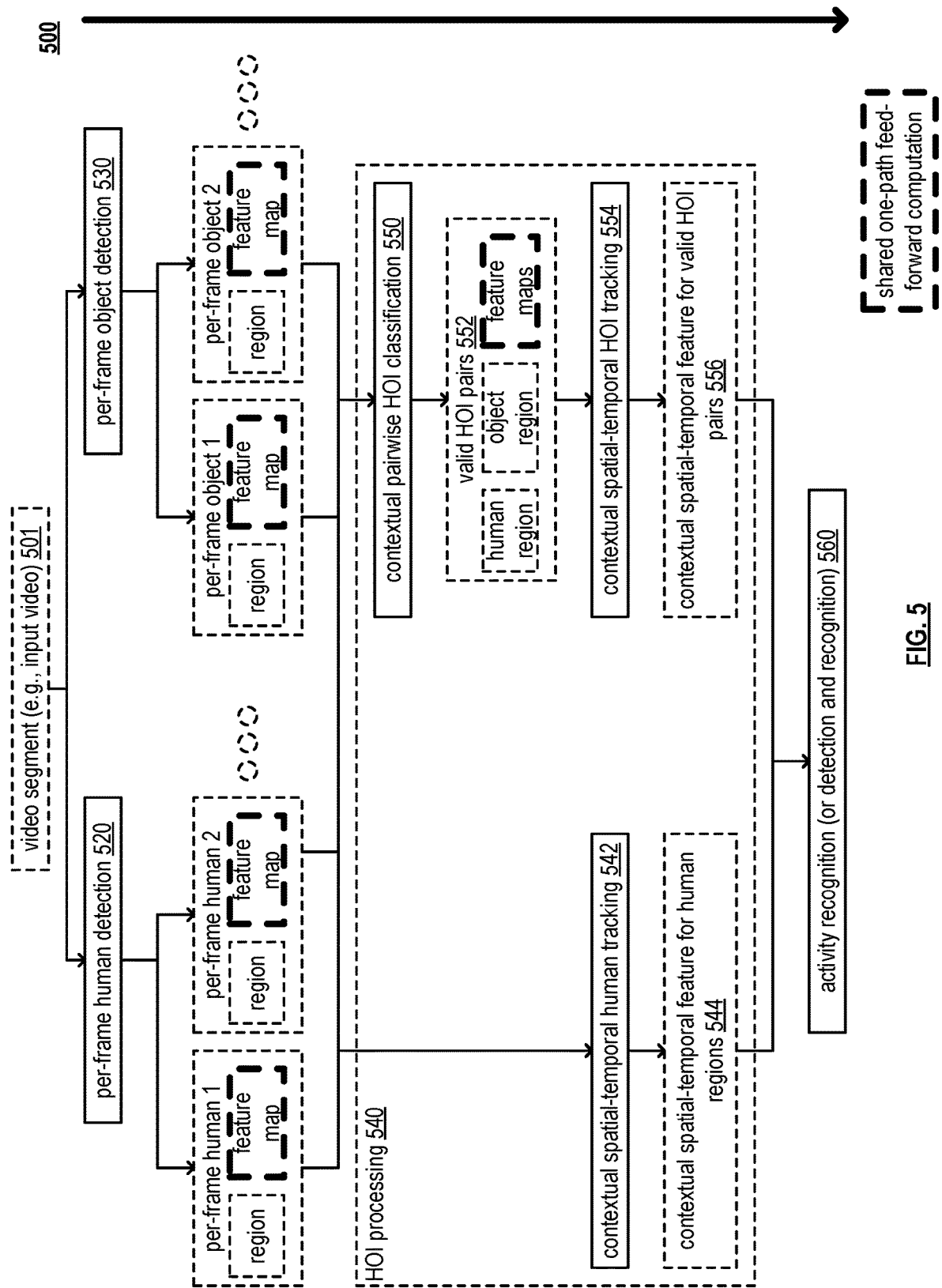
FIG. 5 is a diagram illustrating an embodiment of image and/or video processing that performs joint HOIA learning.

FIG. 5 is a diagram illustrating an embodiment 500 of image and/or video processing that performs joint HOIA learning. Note that such operations as described herein may be performed by a processing circuitry appropriately configured to perform such operations and/or one or more modules thereof that are appropriately configured to perform such operations. Such image and/or video processing operates by receiving as input a video segment 501 (e.g., alternatively referred to as an input video, a video sequence, etc. or equivalent), where each video frame $I_t$ is a color image captured at time t. Note that the video segment may be received from another computing device, from a digital camera (DC) via another computing device and/or one or more network segments, from a DC that is integrated within the computing device, from memory of or associated with one or more computing devices, and/or any other source.

Then, the image and/or video processing operates to detect human and a set of pre-defined objects in the video frame $I_t$. A per-frame human detection module 520 is configured to process the video frame to identify and output detected human regions in the video frame. For instance, each region can be represented by a bounding box $(x_i, y_i, w_i, h_i)$, where $(x_i, y_i)$ and $(w_i, h_i)$ are the center coordinates of the i-th human region in the frame and the width and height of the bounding box, respectively. Also, an H-dim feature vector (when dim indicates dimension and the prefix variable, H, is the dimension size) is generated through the forward computation of the per-frame human detection process. such notation is also used with respect to other vectors herein, such as O-dim, C-dim, etc.

Similarly, a per-frame object detection module 530 is configured to process the video frame to identify and output detected object regions in the video frame, and each region can be represented by a bounding box $(x_j, y_j, w_j, h_j)$ for the j-th object. Also, an O-dim feature vector is generated through the forward computation of the per-frame object detection process. In some examples, a pre-trained human detection network is used to perform human detection in the video frame, and a variety of network structures can be adopted and employed to perform such operations.

In one example, the faster r-cnn (convolutional neural network) network as described in reference [1] (cited below) is used which is trained with publicly available datasets such as MSCOCO as described in reference [2] (cited below) for per-frame human detection.

[1] S. Ren, et al, "Faster R-CNN: Towards Real-Time Object Detection with Region Proposal Networks," NIPS, 2015

[2] T. Lin, et al., "Microsoft COCO: Comment objects in context," arXiv, https://arxiv.org/abs/1405.0312

A pre-trained object detection network can be used to detect a set of pre-defined objects in the video frame, and a variety of network structures can be adopted and employed to perform such operations. Also, in a particular example, the faster r-cnn network such as described in reference [1] is also used here which is trained with either publicly available datasets such as MSCOCO as described in reference [2] or self-collected object data with ground-truth bounding box annotations or a combination of both, for per-frame object detection. In an example of operation and implementation, for each detected human or object region within both human detection and object detection networks, the Region-of-Interest (RoI) pooling layer generates a 512×7×7 dimension feature map, which can be flattened into a 25088-dim feature vector.

A HOI processing module 540 is operative to perform operations related to human tracking and/or HOI tracking. For example, within the HOI processing module 540, a contextual spatial-temporal human tracking module 542 is configured to track (continuously) the detected human regions through the subsequent video frames by and is configured to generate contextual spatial-temporal features for each tracked human regions 544 in a video segment. The video segment consists of a set of video frames within a time period. For example, the entire video can be chopped into 1-sec long video segments, and the contextual spatial-temporal human tracking module 542 can be applied to each video segment, and a contextual spatial-temporal feature can be generated for each tracked human region in each video segment.

In addition, within the HOI processing module 540, the processing based on HOIA of as performed by the per-frame human detection module 520 and the per-frame object detection module 530 is configured output detected human regions and the detected object regions to a contextual pairwise HOI classification module 550 that is configured to generate candidate pairwise HOI features (e.g., based on combined processing of the per-frame human detection module 520 and the per-frame object detection module 530) and further to determine which, if any, of the candidate pairwise HOI features are valid or not for further processing in accordance with a contextual spatial-temporal HOI tracking module 554 that is configured to generate one or more contextual spatial-temporal features for valid HOI pairs 556.

Each contextual spatial-temporal feature for valid HOI pair 556 and/or contextual spatial-temporal features for each tracked human regions 544 can be used for final activity classification in an activity recognition module 560, which determines the final type of the targeted HOI activity and/or detected human. Note the activity recognition module 560 may alternatively perform both detection and recognition on the inputs provided thereto.

This diagram illustrates a system having 2 fully connected layers that are used in accordance with contextual pairwise HOI network layers. In some examples, the contextual pairwise HOI classification training is performed use ground-truth pairs as compared with all possible pairs. In some implementations, this includes a relatively simply network to train, and may be performed using binary supervised classification.

FIG. 6A is a diagram illustrating an embodiment 601 of contextual spatial-temporal human-object interactive (HOI) tracking. A detected and valid HOI pair from (e.g., frame 1 valid pair, frame 2 valid pair, and so on) is tracked throughout a video segment by a bounding box regression and classification module 610, which, in some examples, is implemented a pre-trained contextual HOI regression and classification network 612 to detect and track the HOI region in subsequent frames and outputs the tracked boxes as well as a contextual spatial-temporal feature for each tracked, valid HOI pair 614.

A contextual HOI regression and classification network module (e.g., which is pre-trained in some examples) is implemented to perform regression for a first frame and to generate outputs (x, y, w, h, score) for both human and object in the pair and to output a corresponding feature at the same time. The training of operations may be made in accordance with that used to perform bounding box regression and classification in object detection (e.g., by the bounding box regression and classification module 610). Also, note that a similar framework such as may be used in accordance with object detection may be used here for contextual spatial-temporal HOI tracking and with different network weights.

FIG. 6B is a diagram illustrating an embodiment 602 of contextual spatial-temporal human tracking. In accordance with such contextual spatial-temporal human tracking, a detected human region from a first frame (frame 1 human region) is tracked throughout the video segment (e.g., within subsequent frames such as frame 2 human region, frame 2 human region, and so on) by a bounding box regression and classification module 640, which, in some examples, uses a pre-trained contextual human regression and classification network 630 to detect and track the human region in subsequent frames and outputs the tracked boxes as well as a contextual spatial-temporal feature for each tracked human region. A variety of deep neural network structures can be adopted as the contextual human regression and classification network. In an example, the multi-domain network as described in reference [3] (cited below) is used, where a context-specific set of fully connected layers is used in accordance with various aspects, embodiments, and/or examples presented herein, and their equivalents, followed by a domain-specific last set of fully connected layers in replace of the domain-specific last set of fully connected layers only as described in reference [3]. For example, instead of using a different last set of fully connected layers only for each video (also known as (aka) domain as described in reference [3]), the novel image and/or video processing as presented herein uses a different set of fully connected layers for each HOI activity (aka context), followed by a different last set of fully connected layers for each individual video (aka domain within the context). This means that different videos of the same HOI activity share the same set of fully connected context-dependent layers, and this set of fully connected layers is intended to capture the common characteristics of the tracking targets for videos from the same HOI activity.

[3] H. Nam and B. Han, "Learning multi-domain convolutional neural networks for visual tracking," CVPR 2016.

Figures 7A, 7B:
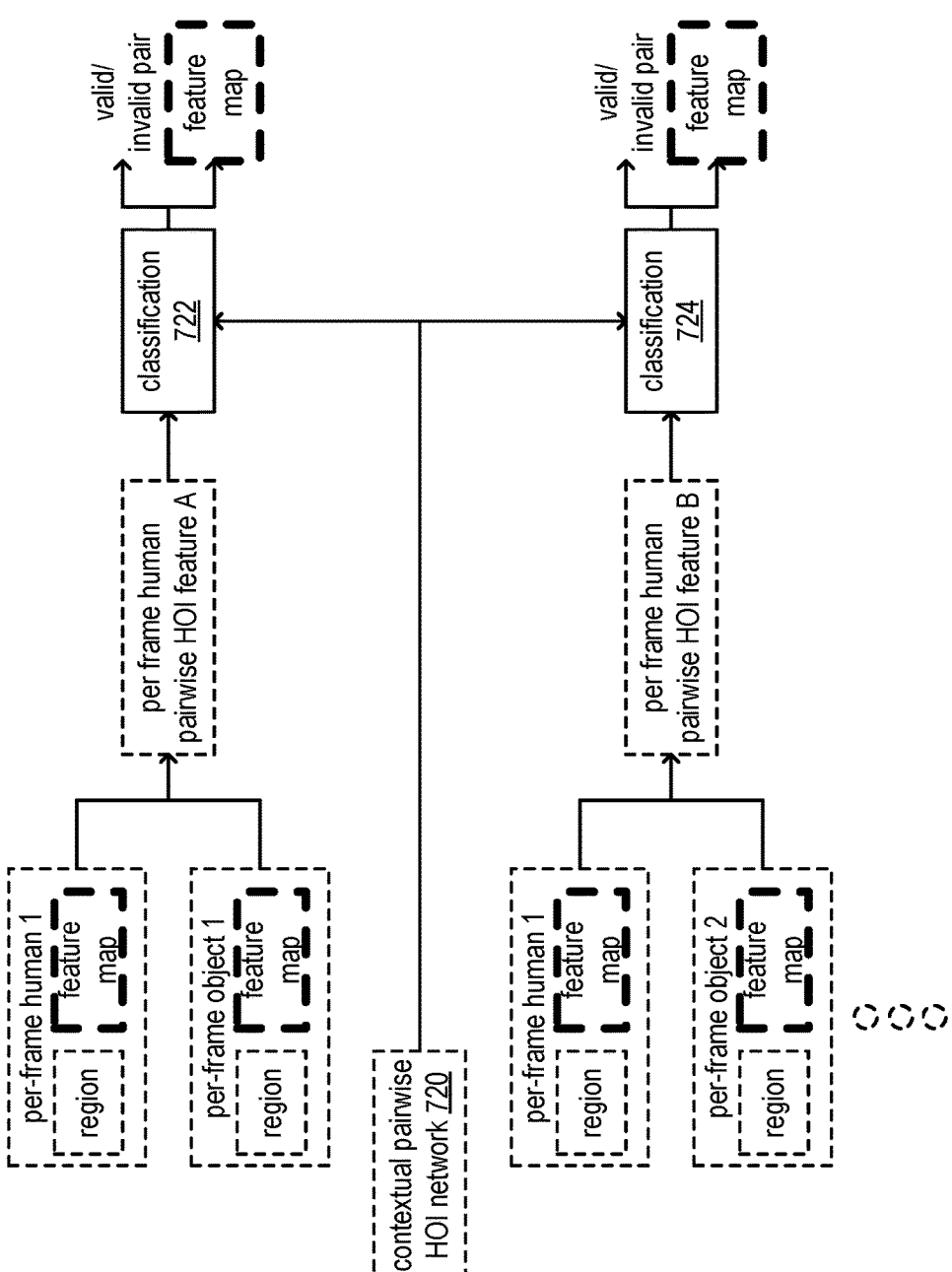
FIG. 7A is a diagram illustrating an embodiment of a contextual regression and classification network structure.
FIG. 7B is a diagram illustrating an embodiment of a contextual pairwise HOI classification process.

FIG. 7A is a diagram illustrating an embodiment 701 of a contextual regression and classification network structure. This diagram illustrates such a network structure as may be used in accordance with contextual regression and classification. The results of processing the video segment based on the convolutional layers 710 is output to the context-specific set of fully connected layers 712 (e.g., with the same weights for the same HOI activity). After forward computation throughout the network, a C-dim contextual spatial-temporal feature vector can be generated from the layer prior to the context-specific set of fully connected layers 714 (e.g., with different weights for different videos) for each tracked human region in each subsequent frame.

Also, the detected human regions and the detected object regions in the video frame $I_t$ generates a set of candidate pairs of human-object region pairs. For each pair, the region bounding boxes and the corresponding H-Dim feature vector for the detected human region and the O-Dim feature vector for the detection object region are used to generate a per-frame pairwise HOI feature. The per-frame pairwise HOI feature is then fed into the contextual pairwise HOI classification module to determine whether the current HOI pair is valid or not for further processing.

FIG. 7B is a diagram illustrating an embodiment 702 of a contextual pairwise HOI classification process. In accordance with such contextual pairwise HOI classification, the per-frame pairwise HOI feature can be generated for each pair of detected human and detected object (e.g., for per frame human pairwise HOI feature A, per frame human pairwise HOI feature B, etc.) by a variety of methods (e.g., including a contextual pairwise HOI network 720). In an example, the corresponding H-Dim feature vector for the detected human region and the O-Dim feature vector for the detection object region can be combined, such as by concatenation, to form an (H+D)-Dim feature vector, and the bounding box of the detected human and the bounding box of the detection object can be concatenated into an 8-Dim location feature vector (e.g., concatenation of two 4-Dim vectors). The (H+D)-Dim feature vector and the 8-Dim location feature vector can be fed into a pre-trained contextual per-frame deep neural network for valid/invalid classification. In an example, the pre-trained contextual per-frame deep neural network has two sets of fully connected layers, one for each input feature vector. Through forward computation over each set of fully connected layers, a valid/invalid classification probability can be computed, and the final valid/invalid probability can be generated by combining the probabilities computed from both sets. For example, classification 722 is configured to determine whether the per frame human pairwise HOI feature A is valid/invalid, and classification 724 is configured to determine whether the per frame human pairwise HOI feature B is valid/invalid. In another embodiment, the (H+D)-Dim feature vector and the 8-Dim location feature vector can be first concatenated and then fed into one set of fully connected layers to compute a valid/invalid classification probability.

Then, each valid human-object pair is continuously tracked through the subsequent video frames by a contextual spatial-temporal HOI tracking module, which will generate contextual spatial-temporal features for each tracked valid human-object pair in the video segment defined in the same way as before for contextual spatial-temporal human tracking. Specifically, the valid human-object pair region from the first frame is tracked throughout the video segment by a bounding box regression and classification module, which uses a pre-trained contextual human-object regression and classification network to detect and track the human-object pair region in subsequent frames and outputs the tracked boxes as well as a contextual spatial-temporal feature for each tracked human-object pair. A variety of deep neural network structures can be adopted as the contextual human-object regression and classification network. In an example, the multi-domain network as described in reference [3] is used, similar to the contextual spatial-temporal human tracking module. After forward computation throughout the network, an E-dim contextual spatial-temporal feature vector can be generated from the layer prior to the context-specific set of fully connected layers for each tracked human-object pair in each subsequent frame.

Finally, the C-dim contextual spatial-temporal feature vector for each tracked human region and the E-dim contextual spatial-temporal feature vector for each tracked human-object pair can be used for final activity classification in the activity recognition module, which determines the final type of the targeted HOI activity. In an example, a deep neural network consisting of a set of fully connected layers is used as the activity recognition model.

FIG. 8A is a diagram illustrating an embodiment of a method 801 for execution by one or more computing devices. The method 801 operates in step 810 by receiving a video segment (e.g., such as via an interface of the computing device that is configured to interface and communicate with a communication network). Note that the video segment may be received from another computing device, from a digital camera (DC) via another computing device and/or one or more network segments, from a DC that is integrated within the computing device, from memory of or associated with one or more computing devices, and/or any other source.

The method 801 continues in step 820 by processing a video frame of the video segment on a per-frame basis and based on joint human-object interactive activity (HOIA) to generate a per-frame pairwise human-object interactive (HOI) feature based on a plurality of candidate HOI pairs. The method 801 then operates in step 830 by processing the per-frame pairwise HOI feature to identify a valid HOI pair among the plurality of candidate HOI pairs. The method 801 also operates in step 840 by tracking the valid HOI pair through subsequent frames of the video segment to generate a contextual spatial-temporal feature for the valid HOI pair to be used in activity detection.

FIG. 8B is a diagram illustrating another embodiment of a method 802 for execution by one or more computing devices. The method 802 operates in step 811 by processing a video frame to identify a detected human region in accordance with human detection based on a pre-trained human detection network. Note that such a pre-trained human detection network may be accessed via a communication network with which the one or more computing devices is connected and/or coupled to and in communication. The method 802 continues in step 821 by processing the video frame to identify a detected object region in accordance with object detection based on a pre-trained object detection network. Also, note that such a pre-trained object detection network may be accessed via a communication network with which the one or more computing devices is connected and/or coupled to and in communication FIG. 8C is a diagram illustrating another embodiment of a method 803 for execution by one or more computing devices. The method 803 operates in step 812 by processing a detected human region and a detected object region within a video frame to generate one or more candidate human-object region pairs. The method 803 continues in step 822 by generating, for a candidate human-object region pair, a per-frame pairwise HOI feature based on a human region bounding box and a human feature vector associated with the detected human region and an object region bounding box and an object feature vector associated with the detected object region Alternative variants of the method 803 operate in step 824 by generating, for a candidate human-object region pair a per-frame pairwise HOI feature based on combined human-object location feature vector that is based on a human region bounding box and an object region bounding box and a combined human-object feature vector that is based on a human feature vector associated with the detected human region and an object feature vector associated with the detected object region.

This disclosure presents, among other things, a novel approach to perform activity detection by learning context (activity) dependent joint spatial-temporal human and object feature. By learning contextual spatial-temporal human and object features, an activity can be better detected than using generic features. Also, this disclosure presents among other things, a novel approach to perform contextual HOI tracking for contextual spatial-temporal HOI feature extraction. The novel joint HOI tracking presented herein allows tracking of multiple human beings and multiple interacting objects. By discriminatively learning joint spatial-temporal HOI features, the extracted contextual spatial-temporal HOI feature is more discriminative for activity detection than static or generically learned HOI features.

The novel processing presented herein allows for contextual spatial-temporal joint human and object feature learning for each individual HOI activity. Also, it provides for context (activity) dependent human object interaction (HOI) tracking for contextual spatial-temporal HOI feature extraction.

Also, the novel processing presented herein including joint HOIA learning, detection, and tracking does not operate based on assumptions of a single human and a single object in the scene. The novel processing presented herein automatically determines human-object pair association. This novel processing is also very fast in terms of computational speed. The novel processing shares computation through different modules of the system by reusing the feed-forwardly computed feature maps. This also provides for very efficient network training with limited data by knowledge transfer such as may be performed using pre-trained human and object detectors transfer knowledge learned from large scale human and object detection data to the current activity detection task.

According to one aspect of the present disclosure, there is provided a method that includes receiving a video segment (e.g., such as via an interface of a computing device that is configured to interface and communicate with a communication network) and processing a video frame of the video segment on a per-frame basis and based on joint human-object interactive activity (HOIA) to generate a per-frame pairwise human-object interactive (HOI) feature based on a plurality of candidate HOI pairs, processing the per-frame pairwise HOI feature to identify a valid HOI pair among the plurality of candidate HOI pairs, and tracking the valid HOI pair through subsequent frames of the video segment to generate a contextual spatial-temporal feature for the valid HOI pair to be used in activity detection.

The interaction and relationship between a human and an object (or one or more objects) is determined jointly by automatically determining human-object pair association. This joint human-object interactive activity (HOIA) learning, detection, and tracking is very fast in terms of computational speed and also operates with very efficient network training with limited data by knowledge transfer such as by using pre-trained human and object detectors.

Optionally, in any of the preceding aspects, the method further includes processing the video frame to identify a detected human region in accordance with human detection based on a pre-trained human detection network via the communication network, and processing the video frame to identify a detected object region in accordance with object detection based on a pre-trained object detection network via the communication network.

Optionally, in any of the preceding aspects, the method further includes processing the detected human region and the detected object region within the video frame to generate a plurality of candidate human-object region pairs, and, for a candidate human-object region pair of the plurality of candidate human-object region pairs, generating the per-frame pairwise HOI feature based on a human region bounding box and a human feature vector associated with the detected human region and an object region bounding box and an object feature vector associated with the detected object region.

Optionally, in any of the preceding aspects, the method further includes processing the detected human region and the detected object region within the video frame to generate a plurality of candidate human-object region pairs, and, for a candidate human-object region pair of the plurality of candidate human-object region pairs, generating the per-frame pairwise HOI feature based on combined human-object location feature vector that is based on a human region bounding box and an object region bounding box and a combined human-object feature vector that is based on a human feature vector associated with the detected human region and an object feature vector associated with the detected object region.

Optionally, in any of the preceding aspects, the method further includes tracking the valid HOI pair through the subsequent frames of the video segment based on a pre-trained contextual human-object regression and classification network via the communication network and to output a tracked human region bounding box and a tracked object region bounding box associated with the valid HOI pair and the contextual spatial-temporal feature for the valid HOI pair.

Optionally, in any of the preceding aspects, a first HOI pair of the plurality of candidate HOI pairs is based on a first context-specific set of fully connected layers of a multi-domain network in the subsequent frames of the video segment, and a second HOI pair of the plurality of candidate HOI pairs is based on a second context-specific set of fully connected layers of the multi-domain network in the subsequent frames of the video segment.

Optionally, in any of the preceding aspects, the method further includes processing the video frame of the video segment on the per-frame basis and based on human detection to generate a human region, and tracking the human region through subsequent frames of the video segment to generate another contextual spatial-temporal feature for the human region to be used in activity detection.

According to another aspect of the present disclosure, there is provided a computing device comprising a communication interface configured to interface and communicate with a communication network, memory that stores operational instructions, and processing circuitry coupled to the communication interface and to the memory to perform any of the proceeding aspects of the method.

According to another aspect of the present disclosure, there is provided a computer readable storage device comprising at least one memory section that stores operational instructions to be executed by processing circuitry of one or more computing devices that cause the one or more computing devices to perform any of the proceeding aspects of the method. Note that such computer readable storage device includes a non-transitory computer readable storage device and/or non-transitory computer readable medium in certain examples.

According to another aspect of the present disclosure, there is provided an apparatus that includes one or more means for performing any of the proceeding aspects of the method.

The disclosure has been described in conjunction with various embodiments. However, other variations and modifications to the disclosed embodiments can be understood and effected from a study of the drawings, the disclosure, and the appended claims, and such variations and modifications are to be interpreted as being encompassed by the appended claims. In the claims, the word "comprising" does not exclude other elements or steps, and the indefinite article "a" or "an" does not exclude a plurality. A single processor, processing circuitry, or other unit may fulfill the functions of several items recited in the claims. The mere fact that certain measures are recited in mutually different dependent claims does not indicate, preclude or suggest that a combination of these measures cannot be used to advantage. Also, a computer program may be stored or distributed on a suitable medium, such as a computer readable storage device, or such as an optical storage medium or a solid-state medium supplied together with, or as part of, other hardware, but may also be distributed in other forms, such as via the Internet or other wired or wireless telecommunication systems.

Also, although the present disclosure has been described with reference to specific features and embodiments thereof, it is evident that various modifications and combinations can be made thereto without departing from scope of the disclosure. The specification and drawings are, accordingly, to be regarded simply as an illustration of the disclosure as defined by the appended claims, and are contemplated to cover any and all modifications, variations, combinations or equivalents that fall within the scope of the present disclosure.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to," "operably coupled to," "coupled to," and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to," "operable to," "coupled to," or "operably coupled to" indicates that an item includes one or more of power connections, input(s), output(s), etc., to perform, when activated, one or more its corresponding functions and may further include inferred coupling to one or more other items. As may still further be used herein, the term "associated with," includes direct and/or indirect coupling of separate items and/or one item being embedded within another item.

As may be used herein, the term "compares favorably" or equivalent, indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

As may also be used herein, the terms "processing module," "processing circuit," "processor," and/or "processing unit" or their equivalents may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

One or more embodiments of an invention have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processing circuitries, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples of the invention. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module includes a processing module, a processor, a functional block, processing circuitry, hardware, and/or memory that stores operational instructions for performing one or more functions as may be described herein. Note that, if the module is implemented via hardware, the hardware may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid state memory, a hard drive memory, cloud memory, thumb drive, server memory, computing device memory, and/or other physical medium for storing digital information.

While particular combinations of various functions and features of the one or more embodiments have been expressly described herein, other combinations of these features and functions are likewise possible. The present disclosure of an invention is not limited by the particular examples disclosed herein and expressly incorporates these other combinations.

What is claimed is:

1. A computing device comprising:
a communication interface configured to interface and communicate with a communication network;
memory that stores operational instructions; and
processing circuitry coupled to the communication interface and to the memory, wherein the processing circuitry is configured to execute the operational instructions to:
process a video frame of a video segment on a per-frame basis and based on joint human-object interactive activity (HOIA) to generate a per-frame pairwise human-object interactive (HOI) feature based on a plurality of candidate HOI pairs, the plurality of candidate HOI pairs based on different context-specific set of fully connected layers of a multi-domain network in subsequent frames of the video segment;
process the per-frame pairwise HOI feature to identify a valid HOI pair among the plurality of candidate HOI pairs; and
track the valid HOI pair through the subsequent frames of the video segment to generate a contextual spatial-temporal feature for the valid HOI pair to be used in activity detection.

2. The computing device of claim 1, wherein the processing circuitry is further configured to execute the operational instructions to:
perform per-frame human detection processing of the video frame to identify a detected human region in accordance with human detection based on a pre-trained human detection network via the communication network; and
perform per-frame object detection processing of the video frame to identify a detected object region in accordance with object detection based on a pre-trained object detection network via the communication network.

3. The computing device of claim 2, wherein the processing circuitry is further configured to execute the operational instructions to:
process the detected human region and the detected object region within the video frame to generate a plurality of candidate human-object region pairs; and
for a candidate human-object region pair of the plurality of candidate human-object region pairs, generate the per-frame pairwise HOI feature based on a human region bounding box and a human feature vector associated with the detected human region and an object region bounding box and an object feature vector associated with the detected object region.

4. The computing device of claim 2, wherein the processing circuitry is further configured to execute the operational instructions to:
process the detected human region and the detected object region within the video frame to generate a plurality of candidate human-object region pairs; and
for a candidate human-object region pair of the plurality of candidate human-object region pairs, generate the per-frame pairwise HOI feature based on combined human-object location feature vector that is based on a human region bounding box and an object region bounding box and a combined human-object feature vector that is based on a human feature vector associated with the detected human region and an object feature vector associated with the detected object region.

5. The computing device of claim 1, wherein the processing circuitry is further configured to execute the operational instructions to:
perform bounding box regression and classification processing to track the valid HOI pair through the subsequent frames of the video segment based on a pre-trained contextual human-object regression and classification network via the communication network and to output a tracked human region bounding box and a tracked object region bounding box associated with the valid HOI pair and the contextual spatial-temporal feature for the valid HOI pair.

6. The computing device of claim 1, wherein:
a first HOI pair of the plurality of candidate HOI pairs is based on a first context-specific set of fully connected layers of a multi-domain network in the subsequent frames of the video segment; and
a second HOI pair of the plurality of candidate HOI pairs is based on a second context-specific set of fully connected layers of the multi-domain network in the subsequent frames of the video segment.

7. The computing device of claim 1, wherein the processing circuitry is further configured to execute the operational instructions to:
process the video frame of the video segment on the per-frame basis and based on human detection to generate a human region; and
track the human region through subsequent frames of the video segment to generate another contextual spatial-temporal feature for the human region to be used in activity detection.

8. The computing device of claim 1, wherein the processing circuitry is further configured to execute the operational instructions to:
process the video frame to identify a detected human region in accordance with human detection based on a pre-trained human detection network via the communication network; and
process the video frame to identify a detected object region in accordance with object detection based on a pre-trained object detection network via the communication network, wherein a HOI pair of the plurality of candidate HOI pairs is based on a unique context-specific set of fully connected layers of a multi-domain network in the subsequent frames of the video segment.

9. The computing device of claim 1 further comprising:
a home service robot, a long-term safety monitoring device, or a life recommendation device.

10. A non-transitory computer readable medium storing computer instructions that, when executed by one or more processing circuitries, cause the one or more processing circuitries to perform the steps of:
process a video frame of a video segment on a per-frame basis and based on joint human-object interactive activity (HOIA) to generate a per-frame pairwise human-object interactive (HOI) feature based on a plurality of candidate HOI pairs, the plurality of candidate HOI pairs based on different context-specific set of fully connected layers of a multi-domain network in subsequent frames of the video segment;
process the per-frame pairwise HOI feature to identify a valid HOI pair among the plurality of candidate HOI pairs; and
track the valid HOI pair through the subsequent frames of the video segment to generate a contextual spatial-temporal feature for the valid HOI pair to be used in activity detection.

11. The non-transitory computer readable medium storing computer instructions of claim 10, wherein the computer instructions, when executed by the one or more processing circuitries, further cause the one or more processing circuitries to perform the steps of:
perform per-frame human detection processing of the video frame to identify a detected human region in accordance with human detection based on a pre-trained human detection network via a communication network that is accessible via one or more communication interfaces of the one or more computing devices; and
perform per-frame object detection processing of the video frame to identify a detected object region in accordance with object detection based on a pre-trained object detection network via the communication network that is accessible via the one or more communication interfaces of the one or more computing devices.

12. The non-transitory computer readable medium storing computer instructions of claim 10, wherein the computer instructions, when executed by the one or more processing circuitries, further cause the one or more processing circuitries to perform the steps of:
process the video frame to identify a detected human region in accordance with human detection based on a pre-trained human detection network via a communication network that is accessible via one or more communication interfaces of the one or more computing devices; and
process the video frame to identify a detected object region in accordance with object detection based on a pre-trained object detection network via the communication network that is accessible via the one or more communication interfaces of the one or more computing devices, wherein a HOI pair of the plurality of candidate HOI pairs is based on a unique context-specific set of fully connected layers of a multi-domain network in the subsequent frames of the video segment.

13. The non-transitory computer readable medium storing computer instructions of claim 10 further comprising:
a home service robot, a long-term safety monitoring device, or a life recommendation device.

14. A method for execution by a computing device, the method comprising:
receiving a video segment via an interface of the computing device that is configured to interface and communicate with a communication network;
processing a video frame of the video segment on a per-frame basis and based on joint human-object interactive activity (HOIA) to generate a per-frame pairwise human-object interactive (HOI) feature based on a plurality of candidate HOI pairs, the plurality of candidate HOI pairs based on different context-specific set of fully connected layers of a multi-domain network in subsequent frames of the video segment;
processing the per-frame pairwise HOI feature to identify a valid HOI pair among the plurality of candidate HOI pairs; and
tracking the valid HOI pair through the subsequent frames of the video segment to generate a contextual spatial-temporal feature for the valid HOI pair to be used in activity detection.

15. The method of claim 14 further comprising:
processing the video frame to identify a detected human region in accordance with human detection based on a pre-trained human detection network via the communication network; and
processing the video frame to identify a detected object region in accordance with object detection based on a pre-trained object detection network via the communication network.

16. The method of claim 15 further comprising:
processing the detected human region and the detected object region within the video frame to generate a plurality of candidate human-object region pairs; and
for a candidate human-object region pair of the plurality of candidate human-object region pairs, generating the per-frame pairwise HOI feature based on a human region bounding box and a human feature vector associated with the detected human region and an object region bounding box and an object feature vector associated with the detected object region.

17. The method of claim 15 further comprising:
processing the detected human region and the detected object region within the video frame to generate a plurality of candidate human-object region pairs; and
for a candidate human-object region pair of the plurality of candidate human-object region pairs, generating the per-frame pairwise HOI feature based on combined human-object location feature vector that is based on a human region bounding box and an object region bounding box and a combined human-object feature vector that is based on a human feature vector associated with the detected human region and an object feature vector associated with the detected object region.

18. The method of claim 14 further comprising:
tracking the valid HOI pair through the subsequent frames of the video segment based on a pre-trained contextual human-object regression and classification network via the communication network and to output a tracked human region bounding box and a tracked object region bounding box associated with the valid HOI pair and the contextual spatial-temporal feature for the valid HOI pair.

19. The method of claim 14, wherein:
a first HOI pair of the plurality of candidate HOI pairs is based on a first context-specific set of fully connected layers of a multi-domain network in the subsequent frames of the video segment; and
a second HOI pair of the plurality of candidate HOI pairs is based on a second context-specific set of fully connected layers of the multi-domain network in the subsequent frames of the video segment.

20. The method of claim 14 further comprising:
processing the video frame of the video segment on the per-frame basis and based on human detection to generate a human region; and
tracking the human region through subsequent frames of the video segment to generate another contextual spatial-temporal feature for the human region to be used in activity detection.

* * * * *

UNITED STATES PATENT AND TRADEMARK OFFICE
CERTIFICATE OF CORRECTION

PATENT NO. : 10,572,723 B2
APPLICATION NO. : 15/835195
DATED : February 25, 2020
INVENTOR(S) : W. Jiang et al.

Page 1 of 1

It is certified that error appears in the above-identified patent and that said Letters Patent is hereby corrected as shown below:

On the Title Page

Other publications (Line 2), please change "Founation" to --Foundation--.

Page 2/other publications (Line 1), please change "Object" to --Objects--.

Page 2/other publications (Line 2), please change "provide" to --provided--.

Signed and Sealed this
Twenty-eighth Day of July, 2020

Andrei Iancu
*Director of the United States Patent and Trademark Office*